United States Patent
Tanaka et al.

(10) Patent No.: US 9,106,808 B2
(45) Date of Patent: Aug. 11, 2015

(54) VIDEO SIGNAL PROCESSING APPARATUS FOR ENDOSCOPE

(71) Applicant: OLYMPUS MEDICAL SYSTEMS CORP., Tokyo (JP)

(72) Inventors: Satoshi Tanaka, Hachioji (JP); Toshihiro Hamada, Fuchu (JP); Yusuke Takenouchi, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 13/856,721

(22) Filed: Apr. 4, 2013

(65) Prior Publication Data

US 2013/0278739 A1    Oct. 24, 2013

Related U.S. Application Data

(63) Continuation of application No. PCT/JP2012/078717, filed on Nov. 6, 2012.

(30) Foreign Application Priority Data

Nov. 16, 2011    (JP) .................................. 2011-250859

(51) Int. Cl.
*A61B 1/04* (2006.01)
*A61B 1/00* (2006.01)
*H04N 7/18* (2006.01)

(52) U.S. Cl.
CPC .............. *H04N 7/18* (2013.01); *A61B 1/00011* (2013.01); *A61B 1/00057* (2013.01); *A61B 1/00009* (2013.01); *A61B 1/00059* (2013.01)

(58) Field of Classification Search
None
See application file for complete search history.

(56) References Cited

U.S. PATENT DOCUMENTS

| | | | | |
|---|---|---|---|---|
| 5,475,420 A | * | 12/1995 | Buchin | 348/72 |
| 5,951,462 A | * | 9/1999 | Yamanaka | 600/118 |
| 8,004,560 B2 | | 8/2011 | Sato et al. | |
| 2002/0196334 A1 | * | 12/2002 | Saito et al. | 348/65 |
| 2003/0122927 A1 | * | 7/2003 | Saito et al. | 348/72 |
| 2008/0183981 A1 | | 7/2008 | Tannai | |

(Continued)

FOREIGN PATENT DOCUMENTS

| | | |
|---|---|---|
| CN | 101842734 A | 9/2010 |
| JP | 10-165367 | 6/1998 |

(Continued)

OTHER PUBLICATIONS

Extended European search report dated May 4, 2015 received in related application EP 12849890.4-1660.

*Primary Examiner* — Jay Patel
*Assistant Examiner* — Reza Aghevli
(74) *Attorney, Agent, or Firm* — Scully, Scott, Murphy & Presser, P.C.

(57) ABSTRACT

A processor includes: a data transmission/reception section that reads parameter data unique to a scope from a ROM provided in the scope; a register communication state determination section that determines whether or not the parameter data read from the data transmission/reception section has an error; and a mute control/color bar control section that if a result of the determination by the register communication state determination section indicates that the parameter data has an error, controls an image processing section according to a type of the parameter data having the error.

7 Claims, 3 Drawing Sheets

(56) References Cited

U.S. PATENT DOCUMENTS

| | | | |
|---|---|---|---|
| 2010/0097453 A1* | 4/2010 | Endo et al. | 348/65 |
| 2010/0128116 A1 | 5/2010 | Sato et al. | |
| 2010/0201795 A1* | 8/2010 | Sato et al. | 348/65 |
| 2011/0069161 A1* | 3/2011 | Ozawa et al. | 348/68 |
| 2011/0085740 A1* | 4/2011 | Liege et al. | 382/254 |
| 2011/0125138 A1* | 5/2011 | Malinouskas et al. | 606/1 |
| 2011/0205552 A1* | 8/2011 | Bendall et al. | 356/606 |
| 2011/0219125 A1* | 9/2011 | Ertas et al. | 709/227 |

FOREIGN PATENT DOCUMENTS

| | | |
|---|---|---|
| JP | 11-169338 | 6/1999 |
| JP | 2000-267018 | 9/2000 |
| JP | 2009-112644 | 5/2009 |

* cited by examiner

FIG.2

| PARAMETER NAME | PARAMETER TYPE | RESPONSE TO PARAMETER ACQUISITION ERROR |
|---|---|---|
| VIDEO INITIALIZATION PARAMETER A | IMAGE OUTPUT RESTRICTION INFORMATION | SINCE PARAMETER IS IMPORTANT FOR ENDOSCOPE IMAGE, BLACK SCREEN IS OUTPUTTED IN CASE OF ERROR. HOWEVER, IF IMAGE OUTPUT RESTRICTION INFORMATION HAS ERROR, COLOR BARS ARE OUTPUTTED AND ERROR MESSAGE IS DISPLAYED. |
| | MIRROR INVERSION INFORMATION | |
| VIDEO INITIALIZATION PARAMETER B | CCD CLIPPING POSITION INFORMATION | IN CASE OF ERROR, ENDOSCOPIC IMAGE IS OUTPUTTED AND ERROR MESSAGE IS DISPLAYED. |
| | CCD PIXEL MISALIGNMENT CORRECTION INFORMATION | |
| VIDEO INITIALIZATION PARAMETER C | SCOPE TYPE INFORMATION | IN CASE OF ERROR, ENDOSCOPIC IMAGE IS OUTPUTTED AND ERROR MESSAGE IS DISPLAYED. |
| | HEATER INFORMATION | |

VIDEO SIGNAL PROCESSING APPARATUS FOR ENDOSCOPE

CROSS REFERENCE TO RELATED APPLICATION

This application is a continuation application of PCT/JP2012/078717 filed on Nov. 6, 2012 and claims benefit of Japanese Application No. 2011-250859 filed in Japan on Nov. 16, 2011, the entire contents of which are incorporated herein by this reference.

BACKGROUND OF THE INVENTION

1. Field of the Invention

The present invention relates to a video signal processing apparatus for an endoscope, and specifically relates to a video signal processing apparatus for an endoscope, the video signal processing apparatus controlling image output according to a type of parameter data having an error.

2. Description of the Related Art

Conventionally, an endoscope apparatus includes a scope (endoscope) including an image pickup device such as a CCD in a distal end portion thereof, and a processor that performs predetermined image processing on an endoscopic image picked up by the image pickup device provided in the scope and displays the endoscopic image on a monitor. The scope and the processor can be detachably attached to each other via, e.g., a connector, enabling different types of scopes to be connected to the processor.

Scopes incorporate, e.g. a ROM with parameters unique to respective scopes stored therein, and when a scope is connected to a processor, the processor acquires parameters unique to the scope by means of communication between the processor and the scope.

For example, Japanese Patent Application Laid-Open Publication No. 11-169338 discloses an endoscope apparatus that detects whether or not connection between a scope and a processor is normal, by means of communication between the scope and the processor. The endoscope apparatus makes a comparison to determine whether or not transmission data transmitted from the scope corresponds to fixed value data stored in the processor, and if the transmission data corresponds to the fixed value data, it is determined that the connection is normal, and if the transmission data does not correspond to the fixed value data, it is determined that the connection has an error. Then, if the scope has a connection error, the processor displays an image indicating that the scope is not connected, on a monitor.

However, even if the scope and the processor are normally connected and unique parameters are read from the scope by means of communication and transmitted to the processor, the read unique parameters may be corrupted by noise such as disturbance. The unique parameters include parameters related to endoscopic image output and parameters not related to endoscopic image output.

SUMMARY OF THE INVENTION

A video signal processing apparatus for an endoscope according an aspect of the present invention provides a video signal processing apparatus for an endoscope, the video signal processing apparatus including an attachable/detachable endoscope including an image pickup section for picking up an image of a subject, and including a signal processing circuit capable of generating a video signal, the video signal processing apparatus including: a data reading section that reads parameter data unique to the endoscope from a memory provided in the endoscope; an error determination section that determines whether or not the parameter data read by the data reading section has an error; and a control section that, if a result of determination by the error determination section indicates that the parameter data has an error, controls the signal processing circuit according to a type of the parameter data having the error.

BRIEF DESCRIPTION OF THE DRAWINGS

FIG. 2 is a diagram for describing types of unique parameter data stored in a ROM.

DETAILED DESCRIPTION OF THE PREFERRED EMBODIMENT

An embodiment of the present invention will be described below with reference to the drawings.

First, a configuration of an endoscope system including a video signal processing apparatus for an endoscope according to an embodiment of the present invention will be described with reference to FIGS. 1 and 2.

Figure 1:
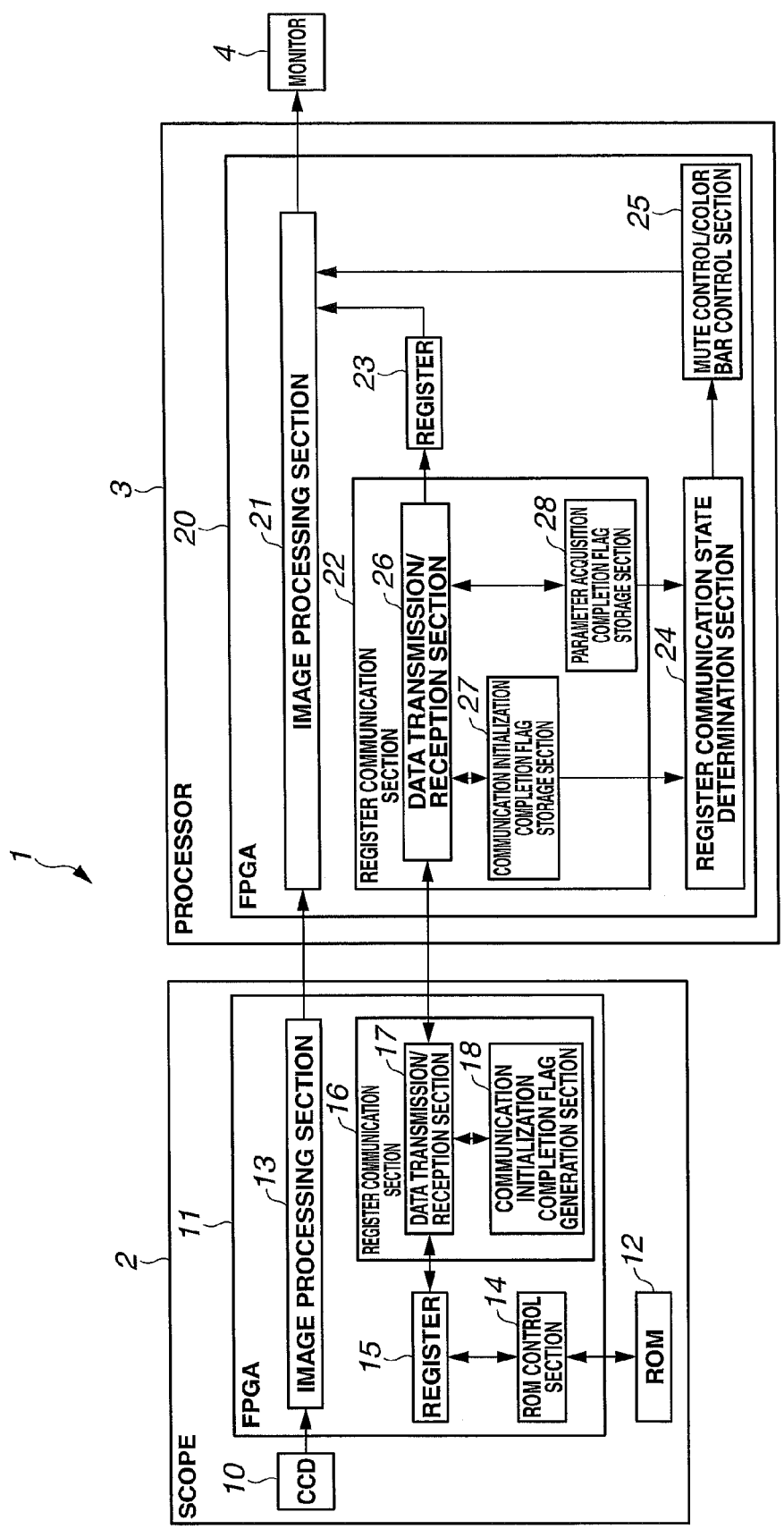
FIG. 1 is a diagram illustrating a configuration of an endoscope system including a video signal processing apparatus for an endoscope according to an embodiment.

FIG. 1 is a diagram illustrating a configuration of an endoscope system including a video signal processing apparatus for an endoscope according to an embodiment, and FIG. 2 is a diagram for describing types of unique parameter data stored in a ROM.

As illustrated in FIG. 1, an endoscope system 1 includes: a scope (endoscope) 2 that picks up an image of a subject; a processor 3, which is a video signal processing apparatus for an endoscope, the processor 3 allowing the scope 2 to be detachably connected thereto and performing predetermined signal processing on an image pickup signal from the scope 2; and a monitor 4 that displays an endoscopic image obtained as a result of the signal processing by the processor 3.

The scope 2 includes a CCD 10, an FPGA 11 and a ROM 12. The FPGA 11 includes an image processing section 13, a ROM control section 14, a register 15 and a register communication section 16. The register communication section 16 includes a data transmission/reception section 17 and a communication initialization completion flag generation section 18.

The processor 3 includes an FPGA 20, and the FPGA 20 includes an image processing section 21, a register communication section 22, a register 23, a register communication state determination section 24 and a mute control/color bar control section 25. The register communication section 22 includes a data transmission/reception section 26, a communication initialization completion flag storage section 27, and a parameter acquisition completion flag storage section 28.

The CCD 10, which is provided at a distal end of a non-illustrated insertion portion to be inserted into a subject, picks up an object image. An image pickup signal resulting from the image pickup is outputted to the image processing section 13 in the FPGA 11.

The image processing section 13 performs image processing for properly transmitting the image pickup signal from the CCD 10 to the processor 3 and transmits the resulting image pickup signal to the image processing section 21 in the processor 3.

In the ROM 12, parameter data unique to the scope 2 are stored. The unique parameter data, which will be described in detail later with reference to FIG. 2, includes video initialization parameters A, B and C. When the scope 2 starts upon the scope 2 being connected to the processor 3, the ROM control section 14 reads the video initialization parameters A to C for the scope 2, which are stored in the ROM 12, and outputs the video initialization parameters A to C to the register 15. The register 15 holds the video initialization parameters A to C from the ROM control section 14 and then outputs the video initialization parameters A to C to the data transmission/reception section 17.

When the scope 2 is connected to the processor 3, enabling image pickup signal output from the CCD 10, the communication initialization completion flag generation section 18 generates a communication initialization completion flag and outputs the communication initialization completion flag to the data transmission/reception section 17.

The data transmission/reception section 17 transmits the communication initialization completion flag generated by the communication initialization completion flag generation section 18 and the video initialization parameters A to C read from the ROM 12 by the ROM control section 14 to the data transmission/reception section 26 in the register communication section 22 of the processor 3.

The data transmission/reception section 26 stores the received communication initialization completion flag in the communication initialization completion flag storage section 27. Also, the data transmission/reception section 26 determines whether or not the received video initialization parameters A to C have been corrupted and stores a video initialization parameter acquisition completion flag for each of the video initialization parameters A to C, the respective video initialization parameter acquisition completion flags indicating whether or not the respective video initialization parameters have been corrupted, in the parameter acquisition completion flag storage section 28. The data transmission/reception section 26 provides a data reading section that reads video initialization parameters A to C stored in the ROM 12 in the scope 2 by means of communication with the scope 2.

Upon the data transmission/reception section 17 in the scope 2 transmitting the video initialization parameters A to C to the data transmission/reception section 26 in the processor 3, the data transmission/reception section 17 generates test data from each of the initialization parameters A to C and transmits the test data. The data transmission/reception section 26 generates test data from each of the received video initialization parameters A to C, and compares the test data with the test data transmitted from the data transmission/reception section 17. Based on a result of the comparison, the data transmission/reception section 26 determines whether or not each of the video initialization parameters A to C has been corrupted.

If the data transmission/reception section 26 determines that the video initialization parameters A to C are normal, the data transmission/reception section 26 outputs the video initialization parameters A to C to the register 23.

The register 23 holds the video initialization parameters A to C outputted from the data transmission/reception section 26 and outputs the video initialization parameters A to C to the image processing section 21.

The image processing section 21 performs predetermined image processing on the image pickup signal from the scope 2 according to the video initialization parameters A to C from the register 23 and outputs the resulting image pickup signal to the monitor 4.

The communication initialization completion flag stored in the communication initialization completion flag storage section 27 and the video initialization parameter acquisition completion flag stored in the parameter acquisition completion flag storage section 28 are inputted to the register communication state determination section 24.

Upon receipt of the communication initialization completion flag, the register communication state determination section 24 determines that image output can be performed, and outputs a control signal for canceling mute of an image signal outputted to the monitor 4 to the mute control/color bar control section 25.

The mute control/color bar control section 25 cancels mute of the image signal outputted to the monitor 4, based on the control signal.

Conventionally, in order to prevent video noise from being displayed on the monitor 4 before image output from the scope 2, video signal mute is performed at a final stage of the processor 3, for example, the image processing section 21. However, since startup time varies depending on the type of the scope connected to the processor 3, in order to make respective scopes output an image in a shortest time period, it is necessary to set mute time for each of the scopes.

Therefore, in the present embodiment, upon power being applied, the communication initialization completion flag generation section 18 in the scope 2 generates a communication initialization completion flag and transmits the communication initialization completion flag to the processor 3. Upon receipt of the communication initialization completion flag from the scope 2, the processor 3 determines that a video image can be outputted to the monitor 4, and cancels mute of a video signal in the image processing section 21. Note that although in the present embodiment, mute is performed in the image processing section 21, which is a final stage of the processor 3, mute may be performed at a final stage of the scope 2, for example, the image processing section 13.

Such configuration enables the processor 3 to cancel mute in a shortest time period for each of scopes, which inevitably vary in startup time due to differences in device configuration, without setting an individual mute time period for each type of scope 2 and switching mute times depending on the type, and output an endoscopic image to the monitor 4 without video noise.

Furthermore, the register communication state determination section 24, which is an error determination section, determines whether or not any of the video initialization parameters A to C has an error, based on the video initialization parameter acquisition completion flag, and outputs a result of the determination, which is provided for selecting an image to be outputted, to the mute control/color bar control section 25.

The mute control/color bar control section 25, which is a control section, generates a control signal for controlling an output image to be outputted to the monitor 4, based on the result of the determination from the register communication state determination section 24, and outputs the control signal to the image processing section 21. More specifically, if the result of the determination from the register communication state determination section 24 indicates that any of the video initialization parameters A to C has an error, the mute control/color bar control section 25 controls the image processing section 21 according to the type of the video initialization parameter A, B or C having the error.

The image processing section 21 selects an output image according to the control signal from the mute control/color bar control section 25 and outputs the output image to the monitor 4.

Note that upon the scope 2 being connected to the processor 3, a scope ID stored in the ROM 12 is read and transmitted to the processor 3. If the processor 3 constantly monitors the scope ID, the processor 3 may detect a wrong scope ID because of disturbance such as static electricity, resulting in the endoscopic image being disturbed.

Therefore, in the present embodiment, once a scope ID is determined after power is applied and after a scope 2 is connected to the processor 3, the processor 3 holds the scope ID as long as the scope ID is not switched to another as a result of, e.g., attachment and detachment of the scope 2 to the processor 3. The processor 3 holding the scope ID as described above prevents detection of a wrong scope ID even if the scope ID is subjected to disturbance after the scope ID is determined.

Such configuration enables the processor 3 to avoid detection of a wrong ID even if a scope ID is subjected to disturbance after the scope ID is determined, enabling avoiding disturbance of an endoscopic image displayed on the monitor 4.

Here, the unique parameter data stored in the ROM 12 in the scope 2 will be described.

As illustrated in FIG. 2, the unique parameter data includes video initialization parameters A, B and C. The video initialization parameter A includes information such as image output restriction information and mirror inversion information. Also, the video initialization parameter B includes information such as CCD clipping position information and CCD pixel misalignment correction information, and the video initialization parameter C includes information such as scope type information and heater information.

The image output restriction information is destination information on a destination of the scope 2. If the processor 3 determines based on the image output restriction information from the scope 2 that the destination information does not correspond to a combination of the scope 2 and the processor 3, the processor 3 does not output an endoscopic image but outputs color bars to the monitor 4.

The mirror inversion information is information used for processing for inverting an image transmitted from a scope 2. Depending on the scope 2, a horizontally-inverted endoscopic image is transmitted to the processor 3 because of a position where the CCD 10 is mounted. Thus, if the processor 3 determines based on the mirror inversion information from a scope 2 that the scope 2 is an inversion scope, inversion processing for, e.g., horizontally or vertically inverting an endoscopic image is performed on the processor 3 side.

Unless the system properly acquires parameter information, i.e., the image output restriction information, the mirror inversion information, etc., of the video initialization parameter A, an endoscopic image cannot properly be outputted, and output of an endoscopic image is prevented. In particular, in the present embodiment, if the image output restriction information has an error, more specifically, if destination information for a scope 2 does not correspond to destination information of the processor 3, color bars are outputted and a message indicating that the scope 2 which is not compatible with the processor 3 is connected. Also, if the mirror inversion information has an error, a mute function is turned on, a black screen is outputted to the monitor 4, and an error message is displayed.

The CCD clipping position information is information indicating which part of effective pixels in the CCD 10 is to be clipped out. Even identical CCDs 10 differ in part of effective pixels in respective CCDs 10 to be clipped out depending on the type of scope 2 (for, e.g., surgical operation, otorhinology or urinary organ). Therefore, the processor 3 acquires clipping information based on the CCD clipping position information from the scope 2 and outputs an endoscopic image to the monitor 4 according to the clipping information.

The CCD pixel misalignment correction information is information indicating an amount of pixel misalignment occurred between two CCDs. If the scope 2 is a scope of a type incorporating a plurality of CCD 10, for example, two CCDs 10 therein, pixel misalignment occurs between the two CCDs 10 because of mounting of the CCDs. Thus, the processor 3 corrects endoscopic images from two CCDs according to the CCD pixel misalignment correction information from the scope 2 and outputs the resulting endoscopic images to the monitor 4.

Since the CCD clipping position information, the CCD pixel misalignment correction information, etc., of the video initialization parameter B causes no serious defect in an endoscopic image even if the processor 3 fails to acquire the parameter and operates with an initial value, an endoscopic image is outputted to the monitor 4 and an error message is displayed.

The scope type information is information used for determining whether or not a scope is a scope having a function of, e.g., LTA-compliant (focus adjusting function). Also, the heater information is parameter information on a heater for defogging.

As with the video initialization parameter B, the scope type information, the heater information, etc., of the video initialization parameter C causes no serious defect in an endoscopic image even if the processor 3 fails to acquire the parameter and operates with an initial value, and thus, the endoscopic image is outputted to the monitor 4 and an error message is displayed.

As described above, in the processor 3 according to the present embodiment, the register communication state determination section 24 determines whether or not any of the above-described video initialization parameters A to C has been corrupted, and based on a result of the determination, the mute control/color bar control section 25 controls an image outputted from the image processing section 21.

Next, an operation of the processor 3 configured as described above will be described.

Figure 3:
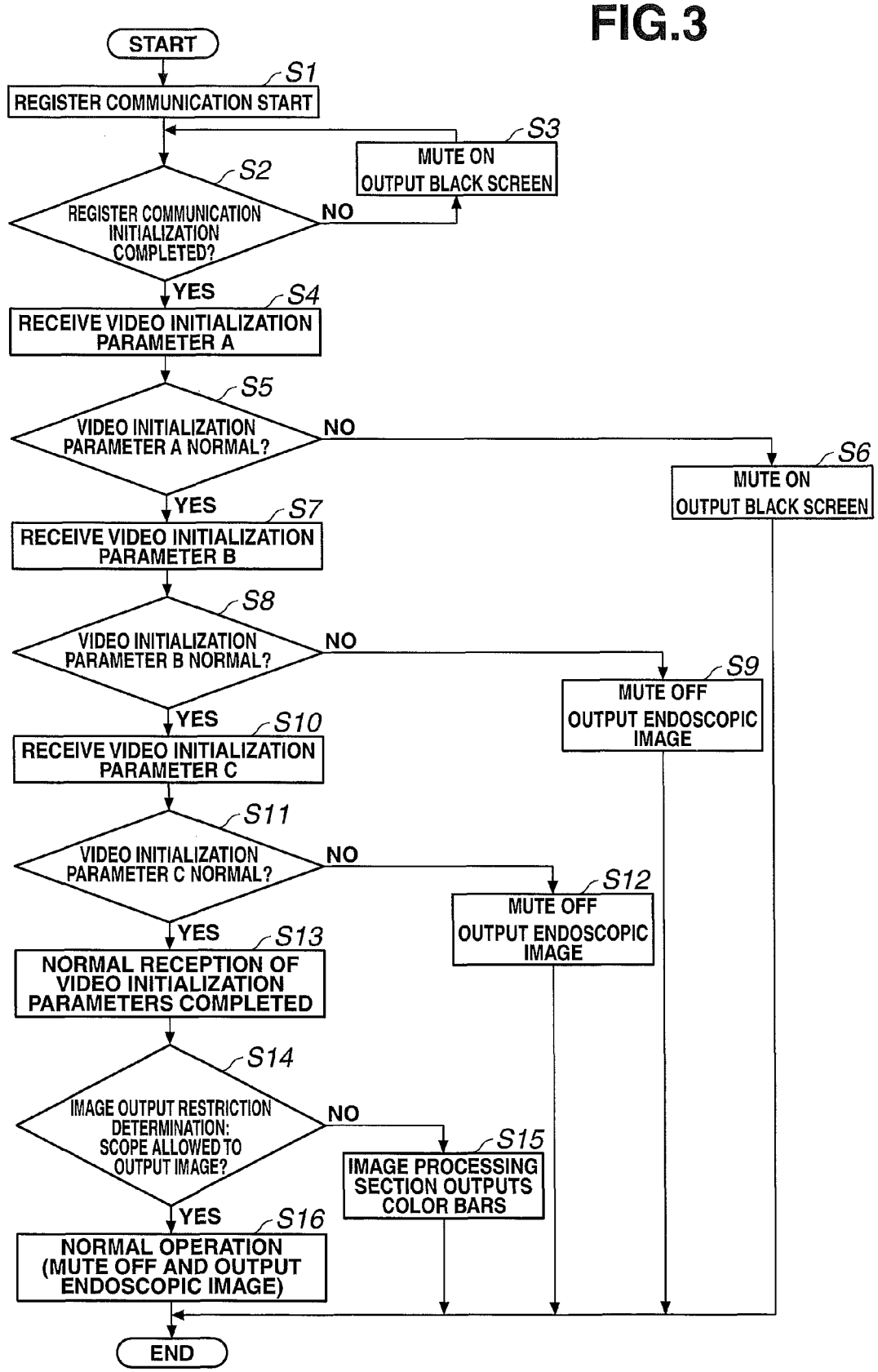
FIG. 3 is a flowchart for describing an example flow of image output processing in a processor 3.

FIG. 3 is a flowchart for describing an example flow of image output processing in the processor 3.

First, upon a scope 2 being connected to the processor 3, register communication starts (step S1), and whether or not register communication initialization has been completed is determined (step S2). If it is determined that register communication initialization has not been completed, a result of the determined is "NO" and thus mute is turned on and a black screen is outputted (step S3). After the processing of step S3 is performed, the processing returns to step S1 and processing similar to the above is repeated. On the other hand, if it is determination that register communication initialization has been completed, the result of the determination is "YES" and the processing advances to step S4.

Next, the video initialization parameter A is received (step S4), and whether or not the video initialization parameter A is normal is determined (step S5). If it is determined that the video initialization parameter A is not normal, a result of the determination is "NO", and thus mute is turned on, a black screen is outputted (step S6) and then the processing ends. On the other hand, if it is determined that the video initialization parameter A is normal, a result of the determination is "YES", and thus, the video initialization parameter B is received (step S7) and whether or not the video initialization parameter B is normal is determined (step S8). If it is determined that the video initialization parameter B is not normal, a result of the determination is "NO" and thus, mute is turned off, an endoscopic image is outputted (step S9), and then the processing ends. On the other hand, if it is determined that the video initialization parameter B is normal, the result of the determination is "YES", and thus, the video initialization parameter C is received (step S10) and whether or not the video initialization parameter C is normal is determined (step S11). If it is determined that the video initialization parameter C is not normal, a result of the determination is "NO", and thus, mute is turned off, an endoscopic image is outputted (step S12), and then the processing ends. On the other hand, if it is determined that the video initialization parameter C is normal, a result of the determination is "YES", and thus, normal reception of the video initialization parameters is completed (step S13).

Next, an image output restriction determination is made, and whether or not the scope 2 connected to the processor 3 is allowed to output an image is determined (step S14). Note that as described above, the image output restriction determination is made using the image output restriction information included in the video initialization parameter A. In step S14, if it is determined that the scope 2 connected to the processor 3 is not allowed to output an image, a result of the determination is "NO" and thus color bars are outputted from the image processing section 21 to the monitor 4 (step S15) and then the processing ends. On the other hand, if it is determined that the scope 2 connected to the processor 3 is allowed to output an image, the result of the determination is "YES", and thus, normal operation is performed, here, mute is turned off, an endoscopic image is outputted (step S16), and the processing ends.

As described above, the processor 3, which is a video signal processing apparatus for an endoscope, determines a type of a parameter that has been corrupted in parameter data (any of video initialization parameters A to C) unique to a scope 2 by means of communication between the scope 2 and the processor 3, and outputs a black image, an endoscopic image or color bars according to a result of the determination.

More specifically, if the video initialization parameter A related to image output has been corrupted, a black image is outputted to the monitor 4, and if either of video initialization parameters B and C not related to image output has been corrupted, an endoscopic image is outputted to the monitor 4, and if a scope 2 allowed to output an image is not connected to the processor 3 (using image output restriction information in the video initialization parameter A for the determination), color bars are outputted to the monitor 4.

As a result, for example, if only the video initialization parameter B or C not related to image output has been corrupted, the processor 3 can prevent endoscopic image output stop.

Accordingly, a video signal processing apparatus for an endoscope according to the present embodiment can output an optimum image according to the type of a corrupted parameter.

Note that regarding the respective steps in the flowchart in the present description, it is possible that the order of the steps to be performed is changed, a plurality of steps are performed simultaneously or the steps are performed in an order that is different in each time the steps are performed, unless such performance runs counter to the nature of the respective steps.

The present invention is not limited to the above-described embodiment and modifications, and various modifications, alterations and the like are possible without departing from spirit of the present invention.

What is claimed is:

1. A video signal processing apparatus for an endoscope, the video signal processing apparatus including an attachable/detachable endoscope including an image pickup section for picking up an image of a subject, and including a signal processing circuit capable of generating a video signal, the video signal processing apparatus comprising:
   a data reading section that reads parameter data unique to the endoscope from a memory provided in the endoscope, the parameter data being used in a process of generating the video signal performed by the signal processing circuit;
   an error determination section that determines whether or not the parameter data read by the data reading section has an error;
   an error data determination section that, if a result of determination by the error determination section indicates that the parameter data has an error, determines a type of the parameter data having the error;
   a control section that controls the signal processing circuit according to a determination result by the error data determination section, and
   a test data generation section that generates test data for each type of parameter data, based on the parameter data from the memory provided in the endoscope, wherein
   the data reading section reads the parameter data from the memory provided in the endoscope and reads the test data generated for each type of parameter data in the endoscope based on the parameter data, and
   the error data determination section determines the type of the parameter data which has the error by comparing the parameter data read from the memory and the test data generated by the test data generation section, for each type of the parameter data.

2. The video signal processing apparatus for an endoscope according to claim 1, wherein if the error data determination section determines that, from among types of the parameter data, an error is included in a piece of the parameter data of a type that hinders proper output of an endoscopic image when the piece of the parameter data has an error, the control section controls the signal processing circuit to output a black image.

3. The video signal processing apparatus for an endoscope according to claim 1, wherein if the error data determination section determines that, from among types of the parameter data, an error is included in a piece of the parameter data of a type that allows proper output of an endoscopic image when the piece of the parameter data has an error, the control section controls the signal processing circuit to output the endoscopic image.

4. The video signal processing apparatus for an endoscope according to claim 1, wherein if the error data determination section determines that from among types of the parameter data, a piece of the parameter data of a type that indicates destination information for the endoscope does not correspond to a piece of parameter data of a type that indicates destination information for the video signal processing apparatus for an endoscope, the control section controls the signal processing circuit to output a color bar.

5. The video signal processing apparatus for an endoscope according to claim 3, wherein if the error data determination section determines that, from among the types of the parameter data, an error is included in a piece of the parameter data of a type that allows proper output of an endoscopic image when the piece of the parameter data has an error, the control section performs control so as to display an error message indicating that the piece of the parameter data has an error together with the endoscopic image outputted by the signal processing circuit.

6. The video signal processing apparatus for an endoscope according to claim 3, wherein a parameter that allows proper output of the endoscopic image includes at least one of information indicating a position where the endoscopic image is displayed in effective pixels of the image pickup section, and, if there are two image pickup sections, information indicating an amount of pixel misalignment occurring between the image pickup sections.

7. The video signal processing apparatus for an endoscope according to claim 2, wherein a parameter that hinders proper output of the endoscopic image includes a parameter indicating whether or not inversion processing for performing vertical or horizontal image inversion is performed on image data expressing the endoscopic image.

\* \* \* \* \*